(12) United States Patent
Arimoto

(10) Patent No.: US 12,209,962 B2
(45) Date of Patent: Jan. 28, 2025

(54) DETECTION METHOD AND DETECTION DEVICE

(71) Applicant: Panasonic Intellectual Property Management Co., Ltd., Osaka (JP)

(72) Inventor: Satoshi Arimoto, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 708 days.

(21) Appl. No.: 17/488,399

(22) Filed: Sep. 29, 2021

(65) Prior Publication Data

US 2022/0018777 A1 Jan. 20, 2022

Related U.S. Application Data

(63) Continuation of application No. PCT/JP2020/018122, filed on Apr. 28, 2020.

(30) Foreign Application Priority Data

May 29, 2019 (JP) .................................. 2019-100628

(51) Int. Cl.
*G01N 21/64* (2006.01)
*B03C 5/00* (2006.01)

(52) U.S. Cl.
CPC .......... *G01N 21/6428* (2013.01); *B03C 5/005* (2013.01); *G01N 2021/6434* (2013.01); *G01N 2021/6497* (2013.01)

(58) Field of Classification Search
CPC ....... G01N 21/6428; G01N 2021/6434; G01N 2021/6497; G01N 27/447; G01N 2030/8813; G01N 33/53; G01N 33/58; B03C 5/005; B03C 2201/26; B03C 5/026; B01D 57/02; C02F 1/469
USPC ........................................................ 435/287.2
See application file for complete search history.

(56) References Cited

U.S. PATENT DOCUMENTS

| | | | |
|---|---|---|---|
| 7,198,702 B1 | 4/2007 | Washizu et al. | |
| 2002/0037499 A1* | 3/2002 | Quake ............... | B01L 3/502753 435/6.19 |
| 2019/0154580 A1 | 5/2019 | Yasuura et al. | |

FOREIGN PATENT DOCUMENTS

| | | | |
|---|---|---|---|
| JP | 2001165906 | * | 6/2001 |
| WO | 2017/187744 | | 11/2017 |

OTHER PUBLICATIONS

International Search Report of PCT application No. PCT/JP2020/018122 dated Aug. 4, 2020.

(Continued)

*Primary Examiner* — Jill A Warden
*Assistant Examiner* — Jacqueline Brazin
(74) *Attorney, Agent, or Firm* — Wenderoth, Lind & Ponack, L.L.P.

(57) ABSTRACT

A target substance detection method includes forming a complex by causing a target substance and a dielectric particle to bind to each other, the dielectric particle being modified with a substance having a property of specifically binding to the target substance; separating the complex and an unbound particle from each other in a liquid by dielectrophoresis, the unbound particle being a dielectric particle not constituting the complex; and detecting the target substance included in the separated complex by using an imaging element.

6 Claims, 8 Drawing Sheets

(56) References Cited

OTHER PUBLICATIONS

Abraham P. Lee et al., "It's Electric: When Technology Gives a Boost to Stem Cell Science", Current Stem Cell Reports 4, Apr. 24, 2018, pp. 116-126.

Yasukawa Tomoyuki, "High sensitivity of rapid immunosensing based on dielectrophoretic manipulation of particles", Report on Shimadzu science foundation (2011), pp. 47-51, 2. experimental procedure, Jan. 31, 2013.

* cited by examiner

FIG. 4
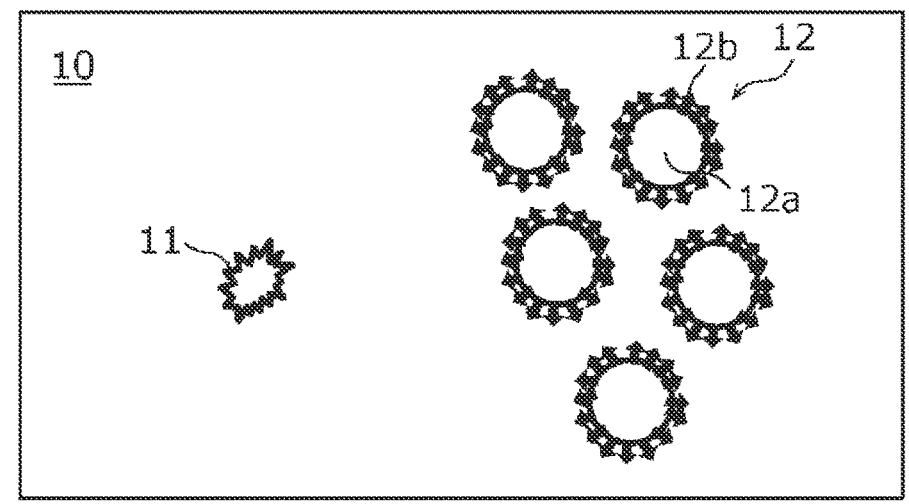
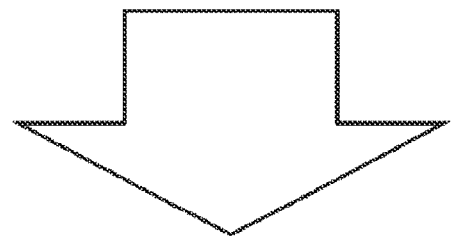
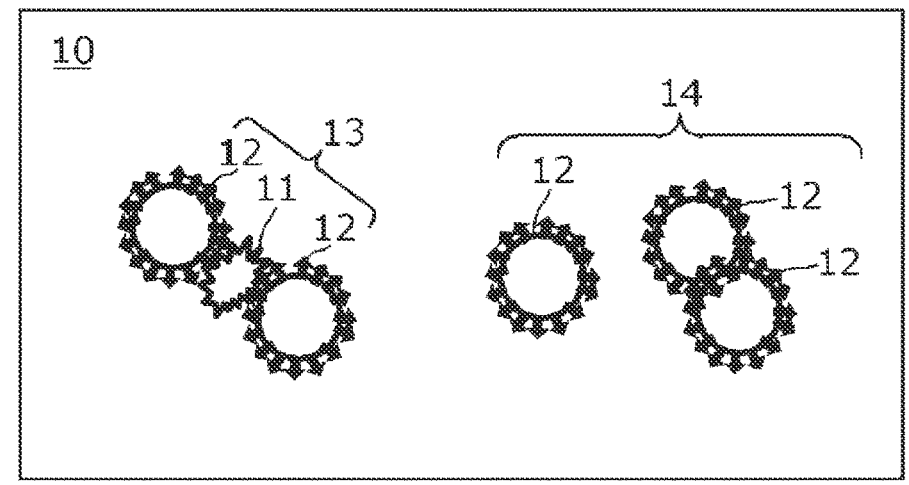

FIG. 8
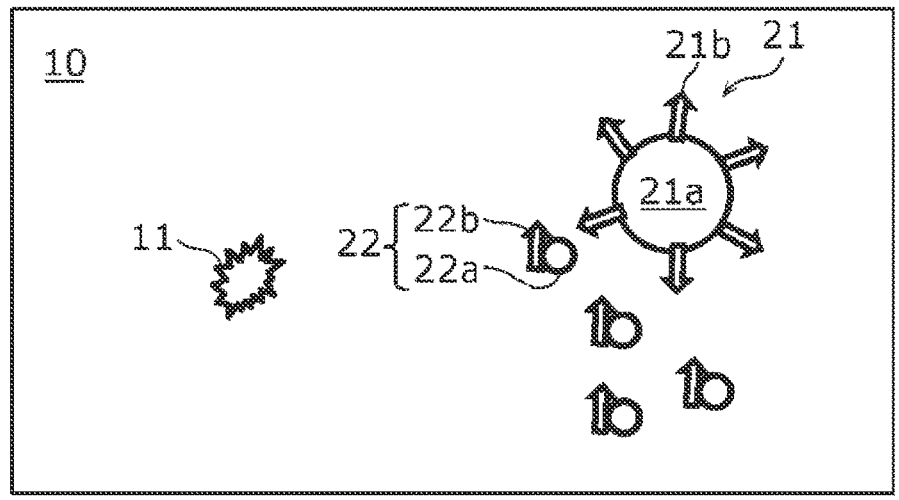
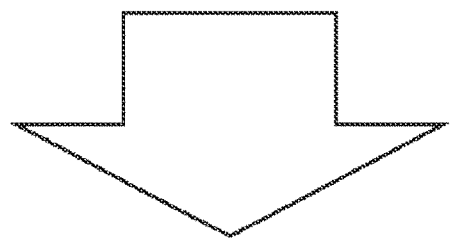
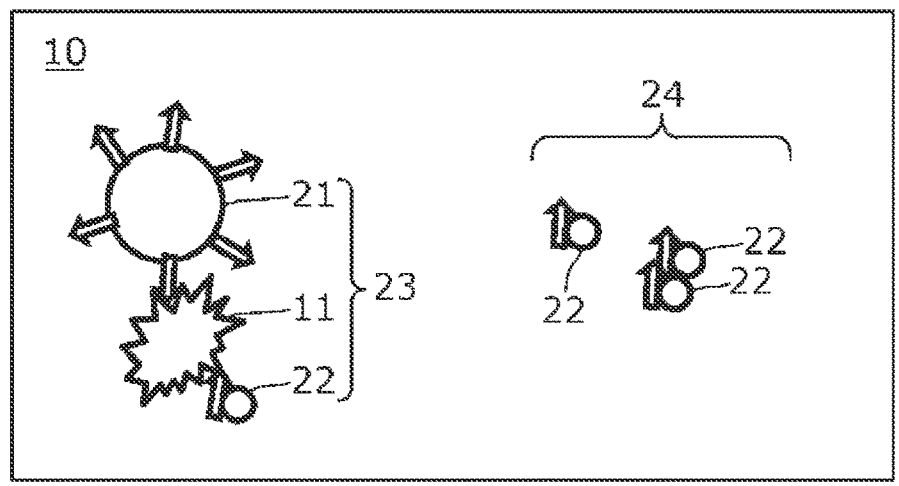

DETECTION METHOD AND DETECTION DEVICE

BACKGROUND

1. Technical Field

The present disclosure relates to a detection method and a detection device for detecting a target substance such as a virus.

2. Description of the Related Art

In the related art, there is provided an optical detection method for highly sensitively detecting a minute target substance by using a near field. For example, in International Publication No. 2017/187744, a target substance is detected by measuring, for example, a decrease caused in an optical signal in response to application of a first magnetic field that causes a bound body, which is formed as a result of the target substance binding to a magnetic particle and a fluorescent particle, to move in a direction away from a surface of a detection plate where a near field is formed.

SUMMARY

However, in International Publication No. 2017/187744, a bound body formed by non-specific adsorption in which a magnetic particle and a fluorescent particle bind to each other without any target substance also moves while emitting fluorescence. Thus, it is difficult to distinguish this bound body from a bound body including the target substance. As a result, false positives in which the target substance is falsely detected because of the bound body not including the target substance may occur, and detection accuracy may decrease.

One non-limiting and exemplary embodiment provides a target substance detection technique capable of reducing false positives caused by non-specific adsorption and improving target substance detection accuracy.

In one general aspect, the techniques disclosed here feature a detection method including forming a complex by causing a target substance and a dielectric particle to bind to each other, the dielectric particle being modified with a substance having a property of specifically binding to the target substance; separating the complex and an unbound particle from each other in a liquid by dielectrophoresis, the unbound particle being a dielectric particle not constituting the complex; and detecting the target substance included in the separated complex by using an imaging element.

The detection method according to the one non-limiting and exemplary embodiment is capable of reducing false positives caused by non-specific adsorption and improving target substance detection accuracy.

It should be noted that general or specific embodiments may be implemented as a system, a device, a method, an integrated circuit, a computer program, a computer-readable recording medium, or any selective combination thereof. Examples of the computer-readable recording medium include a nonvolatile recording medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a diagram illustrating a process of forming a complex in the embodiment;

FIG. 8 is a diagram illustrating a process of forming a complex in a modification of the embodiment.

DETAILED DESCRIPTION

Figure 1:
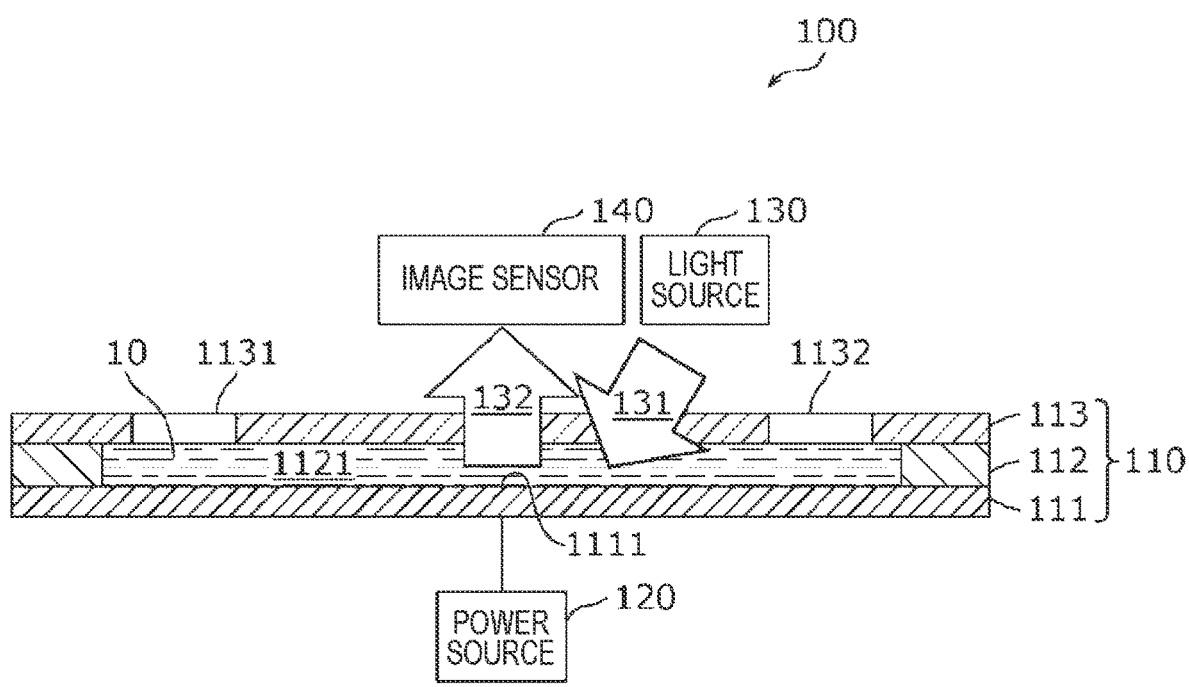
FIG. 1 is a diagram illustrating a configuration of a detection device according to an embodiment.

An embodiment will be specifically described below with reference to the accompanying drawings.

Note that the embodiment described below presents general or specific examples. The numerical values, shapes, materials, components, arranged positions and connections of the components, steps, the order of the steps, etc., described in the following embodiment are merely an example and are not intended to limit the claims. In addition, each drawing does not necessarily present a precise illustration. The same or substantially the same components are denoted by the same reference sign in the drawings, and duplicate description may be omitted or simplified.

Hereinafter, the terms describing relationships between the components, such as "parallel" and "perpendicular", the terms describing shapes of the components, such as "rectangular", and ranges of the numerical values are not used in a strict sense but are used to indicate substantially equivalent ranges with a tolerance of several %, for example.

In addition, hereinafter, detecting a target substance not only indicates finding the target substance to confirm the presence of the target substance but also measuring a quantity of the target substance (for example, the number or concentration) or a range of the quantity.

Embodiment

In an embodiment, complexes and unbound particles are separated from each other in a liquid by dielectrophoresis (DEP), and a target substance included in the separated complexes is detected.

Dielectrophoresis is a phenomenon in which a force is exerted on a dielectric particle that is subjected to a non-uniform electric field. This force does not require the particle to be charged.

A target substance is a substance to be detected and refers to, for example, molecules of a pathogenic protein or the like, a virus (such as a capsid protein), or a bacterium (such as a polysaccharide). The target substance may also be referred to as a substance of interest or a detection target.

An embodiment of a detection device and a detection method that implement detection of a target substance by using dielectrophoresis will be specifically described below with reference to the accompanying drawings.

Configuration of Detection Device 100

A configuration of a detection device 100 will be described first with reference to FIG. 1. FIG. 1 is a diagram illustrating a configuration of the detection device 100 according to an embodiment. As illustrated in FIG. 1, the detection device 100 includes a separator 110, a power source 120, a light source 130, and an imaging element (image sensor) 140.

The separator 110 separates complexes and unbound particles from each other in a liquid by dielectrophoresis. In this embodiment, the separator 110 spatially separates complexes and unbound particles from each other. FIG. 1 illustrates a cross-section of the separator 110.

A complex is a bound body of a target substance and a dielectric particle modified with a substance having a property of specifically binding to the target substance. That is, in the complex, the target substance and the dielectric particle bind to each other with the substance having the property of specifically binding to the target substance therebetween.

A dielectric particle is a particle that can be polarized by an electric field applied thereto. In this embodiment, the dielectric particle includes a fluorescent substance. Note that the dielectric particle is not limited to a particle including a fluorescent substance. For example, a polystyrene particle not including any fluorescent substance may be used as the dielectric particle.

A substance having a property of specifically binding to a target substance (hereinafter, referred to as a specifically binding substance) is a substance that can specifically bind to the target substance. Examples of the specifically binding substance for the target substance include an antibody for an antigen, an enzyme for a substrate or a coenzyme, a receptor for a hormone, protein A or G for an antibody, the avidin family for biotin, calmodulin for calcium, and lectins for sugar.

An unbound particle is a dielectric particle not constituting any complex. That is, the unbound particle is a dielectric particle that has not bound to any target substance. The unbound particle is also referred to as a free (F) component. On the other hand, a dielectric particle included in a complex is also referred to as a bound (B) component.

An internal configuration of the separator 110 will now be described. As illustrated in FIG. 1, the separator 110 includes a first substrate 111, a spacer 112, and a second substrate 113.

The first substrate 111 has an electrode set 1111 to which AC voltages are applied from the power source 120. The electrode set 1111 is capable of producing a non-uniform electric field on the first substrate 111. Details of the electrode set 1111 will be described later with reference to FIG. 2.

The spacer 112 is disposed on the first substrate 111. The spacer 112 has a through hole. The through hole sandwiched between the first substrate 111 and the second substrate 113 forms a channel 1121. A sample liquid 10 that can contain complexes and unbound particles is introduced to the channel 1121.

The second substrate 113, which is, for example, a transparent sheet made of glass or a resin, is disposed on the spacer 112. For example, a polycarbonate substrate can be used as the second substrate 113. The second substrate 113 has a supply hole 1131 and a discharge hole 1132 that are connected to the channel 1121. The sample liquid 10 is supplied to the channel 1121 through the supply hole 1131 and is discharged from the channel 1121 through the discharge hole 1132.

The power source 120 is an AC power source and applies AC voltages to the electrode set 1111 of the first substrate 111. The power source 120 may be any power source capable of supplying AC voltages and is not limited to a power source of a specific kind. The AC voltages may be supplied from an external power source. In this case, the detection device 100 need not include the power source 120.

The light source 130 irradiates the sample liquid 10 in the channel 1121 with excitation light 131. Specifically, the dielectric particles in the sample liquid 10 are irradiated with the excitation light 131. In this embodiment, since the dielectric particles include the fluorescent substance, the fluorescent substance is excited by the excitation light 131 to emit fluorescence 132.

Any known technology can be used as the light source 130 without limitation. For example, a laser such as a semiconductor laser or a gas laser can be used as the light source 130. As a wavelength of the excitation light 131 emitted from the light source 130, a wavelength (for example, 400 nm to 2000 nm) that causes a small interaction with a substance included in a virus may be used. In addition, as the wavelength of the excitation light 131, a wavelength (for example, 600 nm to 850 nm) that can be used by a semiconductor laser may be used.

The detection device 100 need not include the light source 130. For example, when the dielectric particles are large, the dielectric particles need not include the fluorescent substance. In this case, the dielectric particles need not be irradiated with excitation light.

The imaging element 140 captures an image of the complexes separated from the unbound particles by the separator 110 to detect the target substance included in the complexes. In this embodiment, the imaging element 140 captures an image of the fluorescence 132 emitted from the fluorescent substance included in the dielectric particles. An image sensor such as a complementary metal-oxide semiconductor (CMOS) image sensor or a charge-coupled device (CCD) image sensor is used as the imaging element 140.

The detection device 100 may include an optical lens, an optical filter, or an optical lens and an optical lens between the light source 130 and the separator 110, between the separator 110 and the imaging element 140, or between the light source 130 and the separator 110 and between the separator 110 and the imaging element 140. For example, a longpass filter that can block the excitation light 131 emitted from the light source 130 and allow the fluorescence 132 emitted by the fluorescent substance to pass therethrough may be disposed between the separator 110 and the imaging element 140.

Shape and Arrangement of Electrode Set 1111 on First Substrate 111

Figure 2:
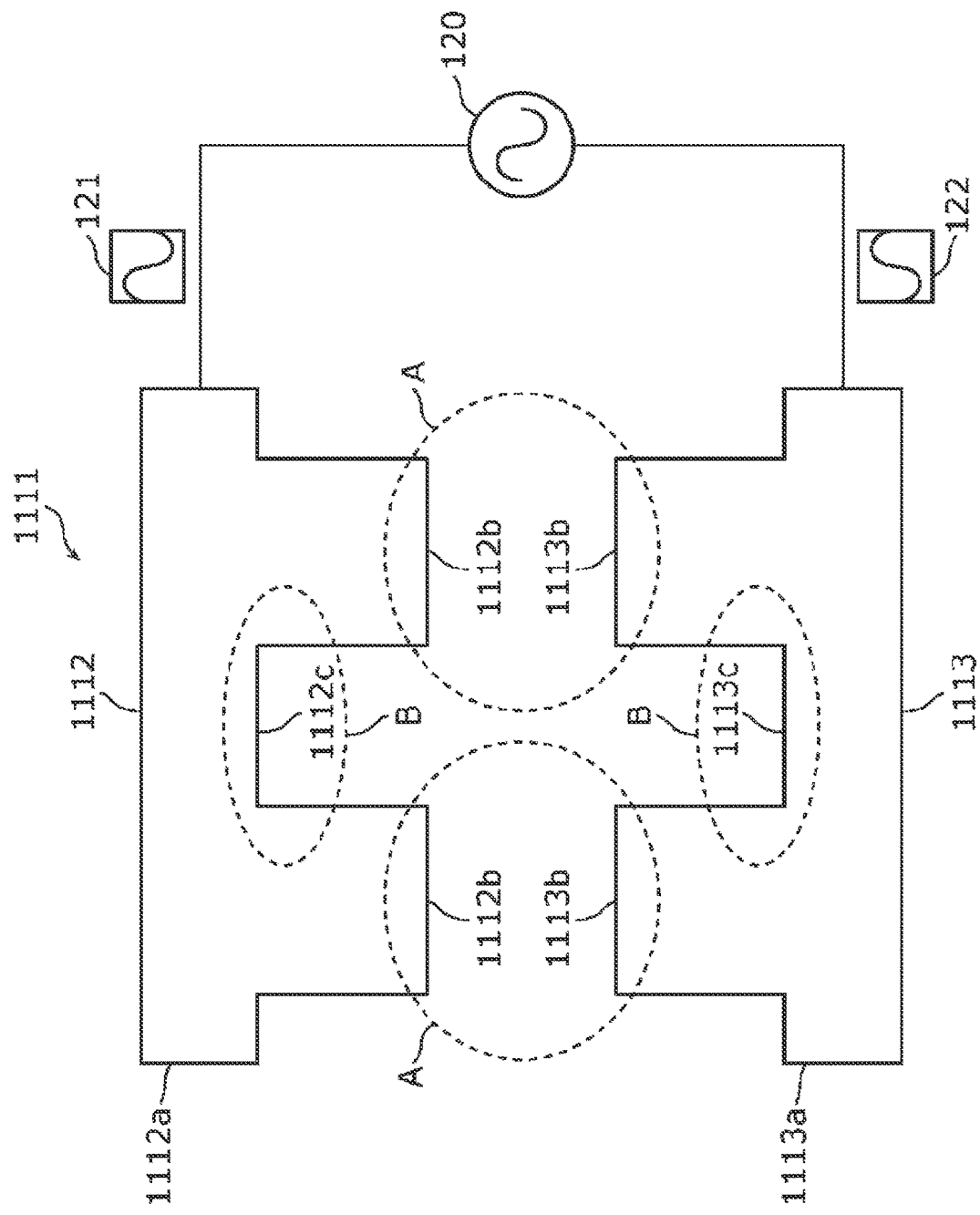
FIG. 2 is a plan view of a first substrate in the embodiment.

A shape and an arrangement of the electrode set 1111 on the first substrate 111 will be described next with reference to FIG. 2. FIG. 2 is a plan view of the first substrate 111 in the embodiment.

As illustrated in FIG. 2, the electrode set 1111 includes a first electrode 1112 and a second electrode 1113 that are disposed on the first substrate 111. Each of the first electrode 1112 and the second electrode 1113 is electrically connected to the power source 120.

The first electrode 1112 includes a base portion 1112a that extends in a first direction (a lateral direction in FIG. 2), and two protruding portions 1112b that protrude from the base portion 1112a in a second direction (a longitudinal direction in FIG. 2) crossing the first direction. A recess portion 1112c is formed between the two protruding portions 1112a, The two protruding portions 1112b and the recess portion 1112c each have, for example, a length of about 5 µm in the first direction and the second direction. Note that the sizes of the two protruding portions 1112b and the recess portion 1112c are not limited to this example.

The second electrode 1113 has substantially the same shape and size as the first electrode 1112. That is, the second electrode 1113 also includes a base portion 1113a that extends in the first direction (the lateral direction in FIG. 2), and two protruding portions 1113b that protrude from the base portion 1113a in the second direction (the longitudinal direction in FIG. 2) crossing the first direction. A recess portion 1113c is formed between the two protruding portions 1113a. The two protruding portions 1113b are disposed to face the two protruding portions 1112b of the first electrode 1112.

AC voltages 121 and 122 are respectively applied to the first electrode 1112 and the second electrode 1113 thus configured, so that a non-uniform electric field is produced on the first substrate 111. The AC voltage 121 applied to the first electrode 1112 and the AC voltage 122 applied to the second electrode 1113 may be substantially the same or may have a phase difference. For example, the AC voltages 121 and 122 may have a phase difference of 180 degrees.

Note that the position of the electrode set 1111 is not limited to on the first substrate 111. It is sufficient that the electrode set 1111 is disposed near the sample liquid 10. The expression "near the sample liquid 10" indicates a range in which an electric field can be produced in the sample liquid 10 by AC voltages applied to the electrode set 1111.

Electric Field Strength Distribution on First Substrate 111

An electric field strength distribution of the non-uniform electric field produced on the first substrate 111 will now be described with reference to FIG. 2.

As illustrated in FIG. 2, first electric field regions A and second electric field regions B are formed on the first substrate 111 by the non-uniform electric field. The first electric field regions A have a relatively large electric field strength, and the second electric field regions B have a relatively small electric field strength. The first electric field regions A are regions each having an electric field strength larger than an electric field strength of the second electric field regions B and each located between the facing protruding portions 1112b and 1113b. The second electric field regions B are regions each having an electric field strength smaller than an electric field strength of the first electric field regions A and located at the respective bottoms of the recess portions 1112c and 1113c.

Detection Method using Detection Device 100

Figure 3:
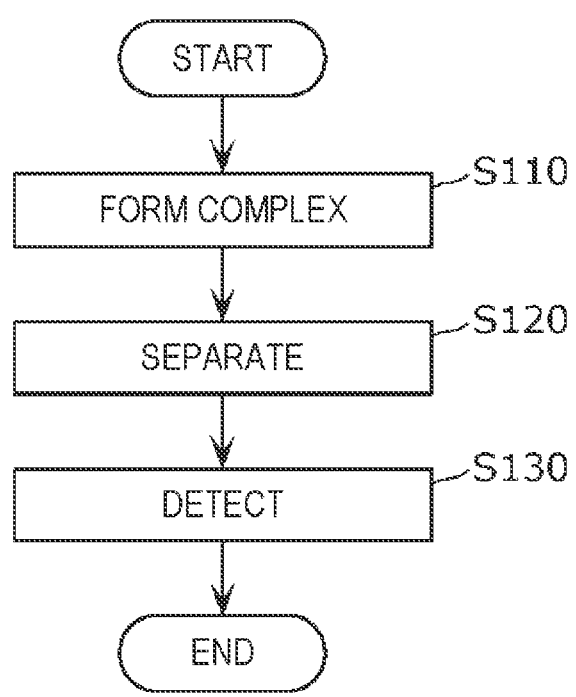
FIG. 3 is a flowchart of a detection method according to the embodiment.

A target substance detection method using the detection device 100 configured in the above-described manner will be described with reference to FIGS. 3 to 5. FIG. 3 is a flowchart of the detection method according to the embodiment.

First, a complex is formed by causing a target substance and a dielectric particle modified with a substance that is capable of specifically binding to the target substance to bind to each other (S110). A process of forming a complex will now be described with reference to FIG. 4. FIG. 4 is a diagram illustrating the process of forming a complex 13 in the embodiment.

As illustrated in FIG. 4(a), antibody-modified dielectric particles 12 are mixed to the sample liquid 10 containing a target substance 11. The antibody-modified dielectric particles 12 are dielectric particles 12a each of which includes the fluorescent substance and is modified with antibodies 12b.

The antibodies 12b are an example of the substance having the property of specifically binding to the target substance 11. In this embodiment, VHH antibodies are adopted as the antibodies 12b. However, the antibodies 12b are not limited to this. The target substance 11, the dielectric particle 12a, and the antibody 12b have sizes of about 100 nm, about 300 nm, and about 5 nm, respectively.

The sample liquid 10 illustrated in FIG. 4(a) is left for a predetermined period at a predetermined temperature. Then, the target substance 11 and the antibody-modified dielectric particles 12 bind to each other by an antigen-antibody reaction, so that the complex 13 is formed as illustrated in FIG. 4(b). In this case, the complex 13 has a size of about 700 nm. The antibody-modified dielectric particles 12 that have not bound to the target substance 11 remain as unbound particles 14 in an isolated or aggregated state.

Note that the structure of the complex 13 illustrated in FIG. 4(b) is merely an example and is not limited to this. For example, the number of antibody-modified dielectric particles 12 included in the complex 13 may be one or may be three or more. For example, the number of bodies of the target substance 11 included in the complex 13 may be two or more.

The description returns to the flowchart of FIG. 3. The complex 13 and the unbound particles 14 are separated from each other in the liquid by dielectrophoresis (S120). Specifically, AC voltages are applied to the electrode set 1111, so that a non-uniform electric field is produced in the sample liquid 10 on the first substrate 111. Consequently, the complex 13 and the unbound particles 14 are subjected to dielectrophoresis, and each of the complex 13 and the unbound particles 14 moves. Note that the antibody-modified dielectric particles 12 in the aggregated state is split into the antibody-modified dielectric particles 12 in the isolated state by dielectrophoresis.

If a frequency of the AC voltages applied to the electrode set 1111 is set to a predetermined frequency at this time, the complex 13 and the unbound particles 14 can be subjected to dielectrophoresis in different directions. For example, if a predetermined frequency with which the complex 13 is subjected to negative dielectrophoresis (nDEP) and the unbound particles 14 are subjected to positive dielectrophoresis (pDEP) is set as the frequency of the AC voltages, the complex 13 moves to the second electric field regions B having a relatively small electric field strength and the unbound particles 14 move to the first electric field regions A having a relatively large electric field strength. Consequently, the complex 13 and the unbound particles 14 are spatially separated from each other.

The predetermined frequency of the AC voltages will now be described with reference to FIG. 5. FIG. 5 is a graph illustrating a set frequency of the AC voltages in the embodiment. In the graph of FIG. 5, the vertical axis represents the real part of the Clausius-Mossotti factor, and the horizontal axis represents the frequency.

If the real part of the Clausius-Mossotti factor is positive, particles are subjected to positive dielectrophoresis. Consequently, the particles move to a region having a larger electric field strength. Conversely, if the real part of the Clausius-Mossotti factor is negative, particles are subjected to negative dielectrophoresis. Consequently, the particles move to a region having a smaller electric field strength.

Figure 5:
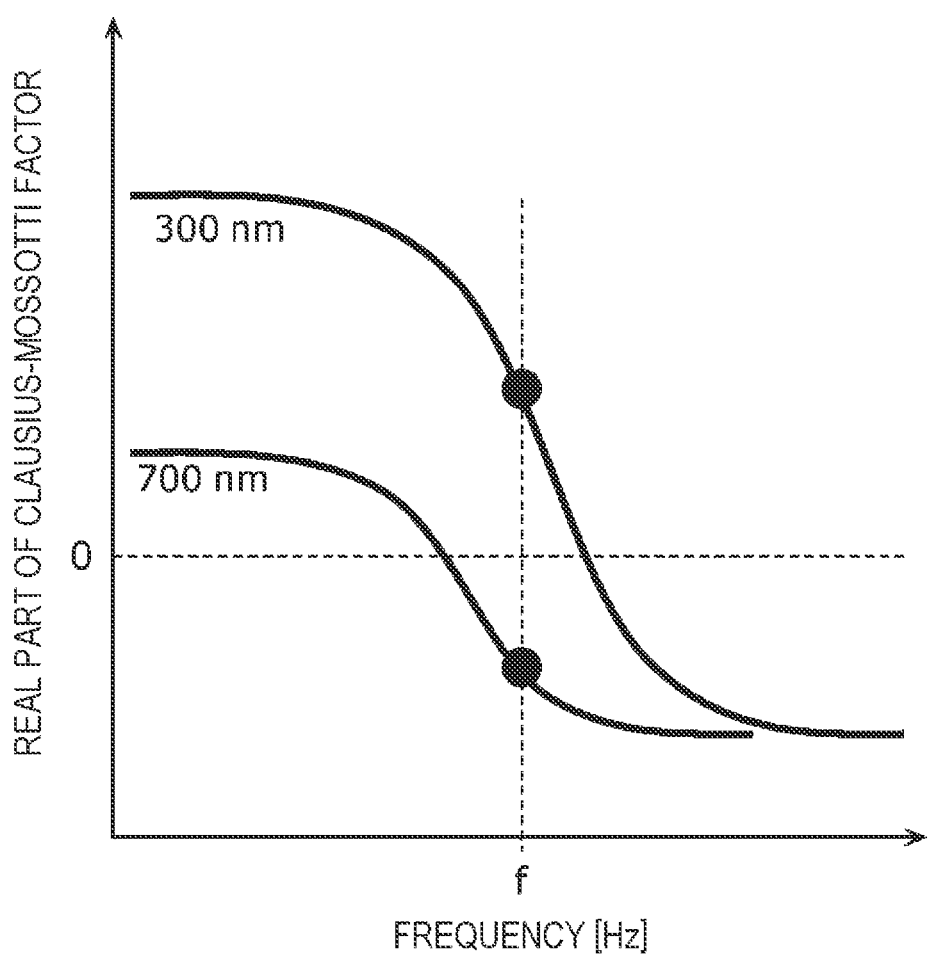
FIG. 5 is a graph illustrating a set frequency of alternating-current (AC) voltages in the embodiment.

As illustrated in FIG. 5, the real part of the Clausius-Mossotti factor is dependent on the particle size and the frequency. At a frequency f, the real part of the Clausius-Mossotti factor is negative for particles having a size of 700 nm which correspond to the complex 13, and is positive for particles having a size of 300 nm which correspond to the unbound particles 14. Accordingly, by setting the frequency f as the predetermined frequency of the AC voltages, the complex 13 can be subjected to negative dielectrophoresis and the unbound particles 14 can be subjected to positive dielectrophoresis.

The description returns to the flowchart of FIG. 3. Lastly, the target substance included in the separated complex 13 is detected (S130). For example, the target substance 11 included in the complex 13 is detected by detecting fluorescence in an image of the second electric field regions B captured by the imaging element 140.

(S110) may include processing of preparing a liquid in which target substances$_{1-n}$ and dielectric particles having surfaces modified with antibodies that are capable of specifically binding to the respective target substances$_{1-n}$ are mixed. These dielectric particles having the modified surfaces may be referred to as surface-modified dielectric particles. The surface-modified dielectric particles include first surface-modified dielectric particles and second surface-modified dielectric particles$_{1-n}$. The number of surface-modified dielectric particles is greater than or equal to (m+n).

(S110) may include processing of leaving the liquid mixture for a predetermined period at a predetermined temperature to form complexes$_{1-n}$. A complex$_i$ includes a target substance$_i$ and a second surface-modified dielectric particle' among the second surface-modified dielectric particles$_{1-n}$. The first surface-modified dielectric particles$_{1-m}$ are not included in any of the complexes$_{1-n}$ and remain in the liquid mixture. The complex$_i$ may include one or more surface-modified dielectric particles that are neither the first surface-modified dielectric particles$_{1-m}$ nor the second surface-modified dielectric particles$_{1-n}$ among the surface-modified dielectric particles.

(S120) may include processing of separating the complexes$_{1-n}$ and the first surface-modified dielectric particles$_{1-m}$ from each other in the liquid with the separator 110 using the AC voltages having the predetermined frequency.

(S130) may include processing of detecting the target substances$_{1-n}$ based on the separated complexes$_{1-n}$.

Note that n, m, and i denote natural numbers, and 1≤i≤n holds.

The target substances$_{1-n}$ indicate the target substance$_1$, . . . , the target substance$_i$, . . . and the target substance$_n$.

The first surface-modified dielectric particles$_{1-m}$ indicate the first surface-modified dielectric particles$_1$, . . . , the first surface-modified dielectric particles$_m$.

The second surface-modified dielectric particles$_{1-m}$ indicate the second surface-modified dielectric particle$_1$, . . . , the second surface-modified dielectric particle$_i$, . . . , the second surface-modified dielectric particle$_n$.

The complexes$_{1-n}$ indicate the complex$_1$, . . . , the complex$_i$, . . . , the complex$_n$.

Advantageous Effects, Etc

As described above, in the detection device 100 and the detection method according to this embodiment, the complex 13 is formed by causing the target substance 11 and the dielectric particle 12a modified with the antibodies 12b to bind to each other; the complex 13 and the unbound particle 14, which is the antibody-modified dielectric particle 12 not constituting the complex 13, are separated from each other in the sample liquid 10 by dielectrophoresis; and the target substance 11 included in the separated complex 13 is detected by using the imaging element 140.

Thus, the complex 13 and the unbound particles 14 can be separated from each other by dielectrophoresis. Further, the unbound particles 14 that have aggregated by non-specific adsorption can be split into individual particles by dielectrophoresis. Therefore, detection accuracy of the target substance 11 included in the complex 13 can be improved, and false positives caused by non-specific adsorption can be reduced. The complex can be caused to move faster by dielectrophoresis than by magnetic forces. Thus, dielectrophoresis can make the detection time of the target substance 11 shorter than the detection time of the target substance 11 using magnetic forces.

In the detection device 100 and the detection method according to this embodiment, in the separating of the complex 13 and the unbound particles 14 from each other, a non-uniform electric field is produced in the sample liquid 10 to subject each of the complex 13 and the unbound particles 14 to the dielectrophoresis.

Thus, separation of the complex 13 and the unbound particles 14 from each other by dielectrophoresis can be easily implemented by producing a non-uniform electric field in the sample liquid 10.

In the detection device 100 and the detection method according to this embodiment, in the separating of the complex 13 and the unbound particles 14 from each other, AC voltages having a predetermined frequency are applied to the electrode set 1111 installed near the sample liquid 10 to produce the non-uniform electric field, and the predetermined frequency is set such that the complex 13 is subjected to negative dielectrophoresis and the unbound particles 14 are subjected to positive dielectrophoresis.

Thus, forces of opposite directions can be applied to the complex 13 and the unbound particles 14 by setting an appropriate frequency for the AC voltages. Consequently, the complex 13 and the unbound particles 14 can be separated from each other more reliably.

In the detection device 100 and the detection method according to this embodiment, in the separating of the complex 13 and the unbound particles 14 from each other, the first electric field regions A and the second electric field regions B having an electric field strength smaller than an electric field strength of the first electric field regions A are formed in the sample liquid 10 by the non-uniform electric field, and the complex 13 moves to the second electric field regions B and the unbound particles 14 move to the first electric field regions A by the dielectrophoresis.

Thus, the complex 13 can be gathered in the second electric field regions B, and the unbound particles 14 can be removed from the second electric field regions B. Therefore, the complex 13 can be detected from the second electric field regions B, and the target substance detection accuracy can be improved.

In the detection device 100 and the detection method according to this embodiment, the dielectric particle 12a includes a fluorescent substance, and in the detecting of the target substance 11, the separated complex 13 is irradiated with the excitation light 131, and the fluorescence 132 emitted by the fluorescent substance included in the complex 13 is detected to detect the target substance 11 included in the complex 13.

Thus, the complex 13 can be detected by detecting the fluorescence 132, and the target substance 11 included in the complex 13 can be easily detected even if the complex 13 is small.

Modifications

The detection device and the detection method according to one or more aspects of the present disclosure have been described above based on the embodiment. However, the present disclosure is not limited to this embodiment. Various modifications conceivable by a person skilled in the art may be made on the embodiment without departing from the gist of the present disclosure, and such modifications may be within the scope of the one or more aspects of the present disclosure.

Figure 6:
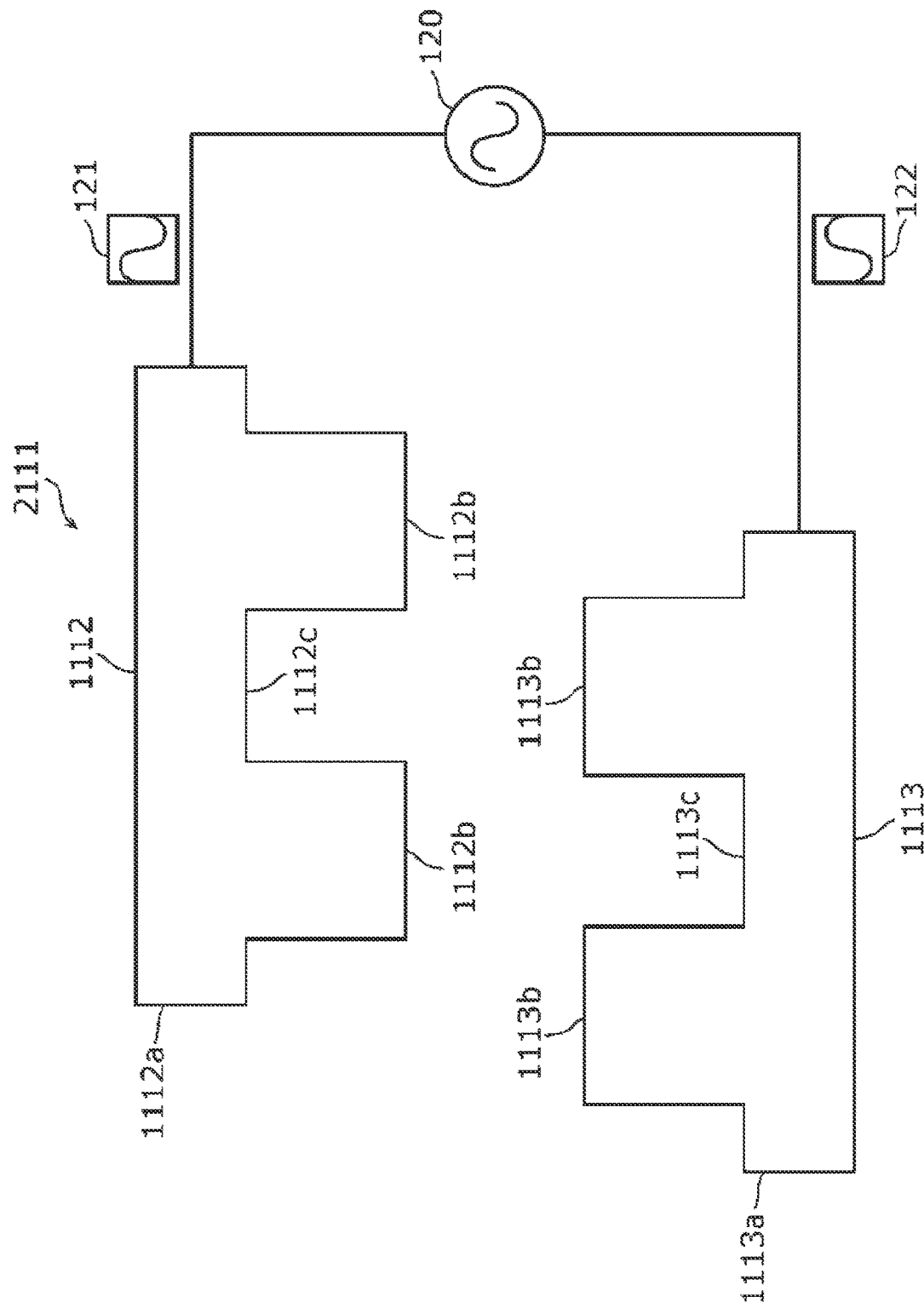
FIG. 6 is a plan view of a first substrate in a modification of the embodiment.

For example, in the embodiment described above, the electrode set 1111 on the first substrate 111 is illustrated in FIG. 2. However, the shape and the arrangement of the electrode set are not limited to this. For example, an electrode set 2111 may be installed on the first substrate 111 as illustrated in FIG. 6. In the electrode set 2111 illustrated in FIG. 6, the protruding portions 1112b of the first electrode 1112 and the protruding portions 1113b of the second electrode 1113 are shifted from each other in the second direction (the lateral direction in FIG. 6). In this modification, the protruding portion 1112b of the first electrode 1112 faces the recess portion 11130 of the second electrode 1113 and the protruding portion 1113b of the second electrode 1113 faces the recess portion 1112c of the first electrode 1112. Even with such an electrode set 2111, a non-uniform electric field can be produced if AC voltages are applied the electrode set 2111.

Figure 7:
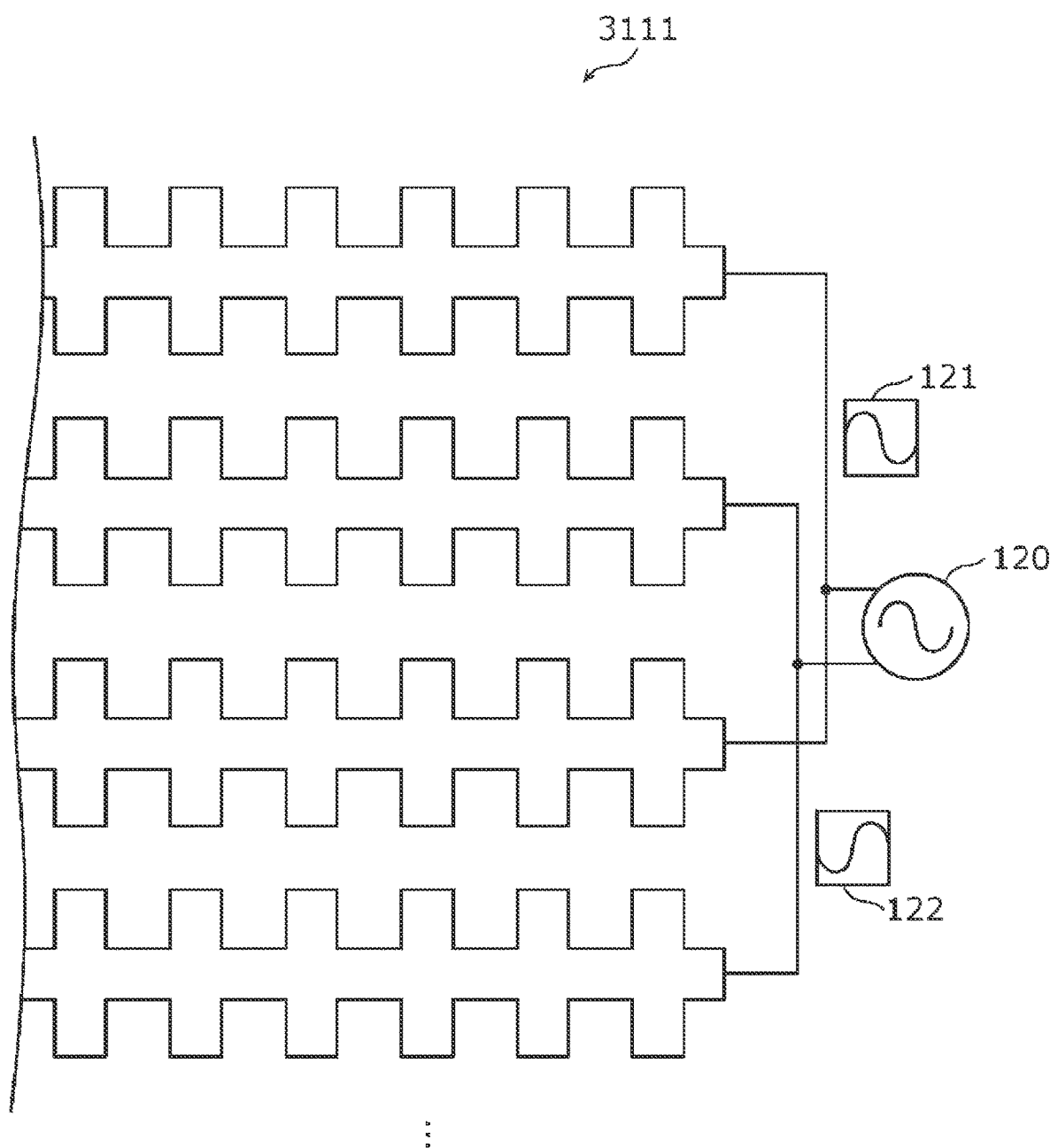
FIG. 7 is a plan view of a first substrate in a modification of the embodiment.

The number of electrodes included in the electrode set is not limited to two and may be three or more. For example, an electrode set 3111 may be installed on the first substrate 111 as illustrated in FIG. 7. The electrode set 3111 illustrated in FIG. 7 includes three or more electrodes, and AC voltages applied to adjacent electrodes have a phase difference. The electrode set 3111 may also be referred to as castellated electrodes.

In the embodiment described above, the complex 13 is illustrated in FIG. 4. However, the structure of the complex is not limited to this. For example, in FIG. 4, the dielectric particle 12a includes the fluorescent substance. Alternatively, a dielectric particle 21a and a fluorescent particle 22a may be separate particles as illustrated in FIG. 8.

As illustrated in FIG. 8(a), an antibody-modified dielectric particle 21 and antibody-modified fluorescent particles 22 are mixed to the sample liquid 10 containing the target substance 11. The antibody-modified dielectric particle 21 is the dielectric particle 21a that has a size of 500 to 1000 nm and is modified with antibodies 21b having a size of about 5 nm. Each of the antibody-modified fluorescent particles 22 is the fluorescent particle 22a that has a size of about 300 nm and is modified with an antibody 22b having a size of about 5 nm. Note that the sizes of the particles and the antibodies are not limited to the aforementioned sizes.

A polystyrene particle can be used as the dielectric particle 21a However, the dielectric particle 21a is not limited to this, VHH antibodies can be used as the antibodies 21b and 22b. However, the antibodies 21b and 22b are not limited to this.

The sample liquid 10 illustrated in FIG. 8(a) is left for a predetermined period at a predetermined temperature. Then, the target substance 11, the antibody-modified dielectric particle 21, and the antibody-modified fluorescent particle 22 bind to each other by an antigen-antibody reaction, so that a complex 23 is formed as illustrated in FIG. 8(b). In this case, the complex 23 has a size of 900 to 1400 nm. The antibody-modified dielectric particles 22 that have not bound to the target substance 11 remain as unbound particles 24 in an isolated or aggregated state.

By making the dielectric particle 21a larger than the fluorescent particle 22a in this manner, a difference between the size of the complex 23 and the size of the unbound particle 24 can be increased. Consequently, the complex 23 and the unbound particles 24 can be separated from each other by dielectrophoresis more reliably.

The detection device 100 can be used as a detection device for detecting a virus such as an influenza virus.

What is claimed is:

1. A detection method comprising:
    forming a complex by causing a target substance and a dielectric particle to bind to each other, the dielectric particle being modified with a substance having a property of specifically binding to the target substance, the dielectric particle including a fluorescent substance;
    separating the complex and an unbound particle from each other in a liquid by dielectrophoresis, the unbound particle being a dielectric particle not constituting the complex, thereby the unbound particle being located in a first electric field region corresponding to a region provided between a protruding part of a first electrode included in an electrode pair and a protruding part of a second electrode included in the electrode pair and the complex being located in a second electric field region corresponding to a region provided at a bottom of a recessed part of the first electrode and a region provided at a bottom of a recessed part of the second electrode;
    capturing fluorescence emitted by the fluorescent substance included in the complex located in the second electric field region on an image when the separated complex is irradiated with excitation light; and
    detecting the target substance included in the separated complex located in the second electric field region in the image.

2. The detection method according to claim 1, wherein in the separating of the complex and the unbound particle from each other, a non-uniform electric field is produced in the liquid to subject each of the complex and the unbound particle to the dielectrophoresis.

3. The detection method according to claim 2, wherein
    in the separating of the complex and the unbound particle from each other,
    an AC voltage having a predetermined frequency is applied to the electrode pair installed near the liquid to produce the non-uniform electric field, and
    the predetermined frequency is set such that the complex is subjected to negative dielectrophoresis and the unbound particle is subjected to positive dielectrophoresis.

4. The detection method according to claim 3, wherein
    in the separating of the complex and the unbound particle from each other,
    the first electric field region and the second electric field region having an electric field strength smaller than an electric field strength of the first electric field region are formed in the liquid by the non-uniform electric field, and
    the complex moves to the second electric field region and the unbound particle moves to the first electric field region by the dielectrophoresis.

5. A detection device comprising:
    a liquid including a complex and an unbound particle;
    a dielectrophoresis separator including an electrode pair, the separator configured to separate the complex and the unbound particle from each other in the liquid by dielectrophoresis, the complex being a complex of a target substance that has bound to a dielectric particle modified with a substance having a property of specifically binding to the target substance, the dielectric particle including a fluorescent substance, the unbound particle being a dielectric particle not constituting the complex, thereby the unbound particle being located in a first electric field region corresponding to a region provided between a protruding part of a first electrode included in the electrode pair and a protruding part of a second electrode included in the electrode pair and the complex being located in a second electric field region corresponding to a region provided at a bottom of a recessed part of the first electrode and a region provided at a bottom of a recessed part of the second electrode;

a light source that irradiates excitation light;

an imaging element configured to capture fluorescence emitted by the fluorescent substance included in the complex located in the second electric field region on an image when the separated complex is irradiated with excitation light by the light source and the imaging element is also configured to detect the target substance included in the separated complex located in the second electric field region in the image.

6. A detection device comprising:

a power source that applies an AC voltage having a predetermined frequency;

a liquid including $complexes_{1-n}$ and first surface-modified dielectric $particles_{1-m}$;

a separator including an electrode pair, the separator configured to separate the $complexes_{1-n}$ and the first surface-modified dielectric $particles_{1-m}$ from each other in the liquid by using the AC voltage having a predetermined frequency, thereby the first surface-modified dielectric $particles_{1-m}$ being located in a first electric field region corresponding to a region provided between a protruding part of a first electrode included in the electrode pair and a protruding part of a second electrode included in the electrode pair and the $complexes_{1-n}$ being located in a second electric field region corresponding to a region provided at a bottom of a recessed part of the first electrode and a region provided at a bottom of a recessed part of the second electrode;

a light source that irradiates excitation light;

an imaging element configured to capture fluorescence emitted by a fluorescent substance included in the $complexes_{1-n}$ located in the second electric field region on an image when the separated complex is irradiated with excitation light by the light source and the imaging element is also configured to detect target $substances_{1-n}$ based on the separated $complexes_{1-n}$, located in the second electric field region in the image wherein the first surface-modified dielectric $particles_{1-m}$ are not included in the $complexes_{1-n}$, and a $complex_i$ includes a target $substance_i$ and a second surface-modified dielectric $particle_i$ among second surface-modified dielectric $particles_{1-n}$, and the first surface-modified dielectric $particles_{1-m}$ and the second surface-modified dielectric $particles_{1-n}$ are modified with antibodies that are capable of specifically binding to the corresponding target $substances_{1-n}$, where n, m, and i are natural numbers and $1 \leq i \leq n$ holds.

* * * * *